(12) United States Patent
Vail et al.

(10) Patent No.: US 10,562,997 B2
(45) Date of Patent: Feb. 18, 2020

(54) METHOD OF PURIFYING A BIOLOGICAL COMPOSITION AND ARTICLE THEREFOR (71) Applicant: 3M INNOVATIVE PROPERTIES COMPANY, St. Paul, MN (US)

(72) Inventors: Andrew W. Vail, Woodbury, MN (US); Jerald K. Rasmussen, Woodville, WI (US); John J. Schmidt, Eagan, MN (US); Ali E. Ozcam, St. Paul, MN (US); Jonathan F. Hester, Hudson, WI (US); Gregory M. Jellum, Marine on St. Croix, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 135 days.

(21) Appl. No.: 15/549,268

(22) PCT Filed: Mar. 17, 2016

(86) PCT No.: PCT/US2016/022842
§ 371 (c)(1),
(2) Date: Aug. 7, 2017

(87) PCT Pub. No.: WO2016/153915
PCT Pub. Date: Sep. 29, 2016

(65) Prior Publication Data
US 2018/0066095 A1 Mar. 8, 2018

Related U.S. Application Data

(60) Provisional application No. 62/137,365, filed on Mar. 24, 2015.

(51) Int. Cl.
*C12N 15/10* (2006.01)
*C12Q 1/6806* (2018.01)
(Continued)

(52) U.S. Cl.
CPC ........ *C08F 255/02* (2013.01); *C12N 15/1017* (2013.01); *C12Q 1/6806* (2013.01); *G01N 1/4077* (2013.01); *G01N 2001/4088* (2013.01)

(58) Field of Classification Search
None
See application file for complete search history.

(56) References Cited

U.S. PATENT DOCUMENTS 4,340,057 A 7/1982 Bloch
4,551,307 A 11/1985 Koyama
(Continued)

FOREIGN PATENT DOCUMENTS

JP H10-279713 10/1998
WO WO 2009-086347 7/2009
(Continued)

OTHER PUBLICATIONS

Di Risio, "Adsorption and Inactivation Behavior of Horseradish Peroxidase on Cellulosic Fiber Surfaces", Journal of Colloid and Interface Science, 2009, vol. 338, No. 2, pp. 410-419, XP026501847.
(Continued)

*Primary Examiner* — Bradley R Spies
(74) *Attorney, Agent, or Firm* — Bradford B. Wright (57) ABSTRACT

A method of purifying a biological composition includes: disposing loose cationic ligand-functionalized staple fibers and a biological composition within a mixing volume of a vessel; agitating the biological composition and the loose cationic ligand-functionalized staple fibers while they are in intimate contact with each other within the mixing volume to provide modified fibers and a purified biological composition; and separating at least a portion of the purified biological composition from the modified fibers and any loose cationic ligand-functionalized staple fibers with which it is in contact. The loose cationic ligand-functionalized
(Continued)

staple fibers have a modified surface layer comprising a grafted acrylic polymer comprising 10 to 100 percent by weight of a cationically-ionizable monomer unit. An article for purifying a biological composition includes: a vessel having a mixing volume disposed therein; and the loose cationic ligand-functionalized staple fibers disposed within the mixing volume.

18 Claims, 1 Drawing Sheet

(51) Int. Cl.
*C08F 255/02* (2006.01)
*G01N 1/40* (2006.01)

(56) References Cited

U.S. PATENT DOCUMENTS

| | | |
|---|---|---|
| 4,618,533 A | 10/1986 | Steuck |
| 4,885,086 A | 12/1989 | Miura |
| 5,061,751 A | 10/1991 | Patton |
| 5,202,025 A | 4/1993 | Onishi |
| 5,344,701 A | 9/1994 | Gagnon |
| 5,350,805 A | 9/1994 | Lin |
| 5,531,900 A | 7/1996 | Raghavan |
| 6,007,803 A | 12/1999 | Mandeville, III |
| 6,818,038 B2 | 11/2004 | Sugo |
| 6,861,001 B2 | 3/2005 | Lee |
| 7,160,464 B2 | 1/2007 | Lee |
| 7,533,417 B2 | 5/2009 | Belz |
| 8,328,023 B2 | 12/2012 | Weiss |
| 8,329,034 B2 | 12/2012 | Waller, Jr. |
| 8,356,717 B2 | 1/2013 | Waller, Jr. |
| 8,377,672 B2 | 2/2013 | Rasmussen |
| 8,435,776 B2 | 5/2013 | Rasmussen |
| 8,551,894 B2 | 10/2013 | Seshadri |
| 8,586,338 B2 | 11/2013 | Etzel |
| 8,652,582 B2 | 2/2014 | Bothof |
| 8,906,645 B2 | 12/2014 | Swanson |
| 2001/0018513 A1 | 8/2001 | Baker |
| 2003/0082565 A1* | 5/2003 | Jang .................. C12N 15/1013 435/6.13 |
| 2010/0155323 A1 | 6/2010 | Weiss |
| 2010/0210160 A1 | 8/2010 | Hester |
| 2011/0033633 A1* | 2/2011 | Bothof .................. B01J 20/285 427/496 |
| 2011/0201078 A1* | 8/2011 | Rasmussen .......... C08F 220/60 435/183 |
| 2012/0252091 A1 | 10/2012 | Rasmussen |
| 2013/0266951 A1* | 10/2013 | Will .................. C12N 15/1006 435/6.12 |
| 2014/0057388 A1 | 2/2014 | Hwang |
| 2014/0170667 A1* | 6/2014 | Dykes ................ C12N 15/1013 435/6.12 |

FOREIGN PATENT DOCUMENTS

| | | |
|---|---|---|
| WO | WO 2013-184366 | 12/2013 |
| WO | WO 2014-204763 | 12/2014 |

OTHER PUBLICATIONS

Won, "Cationic Polymer-Immobilized Polysulfone-based Fibers as High Performance Sorbents for Pt(IV) Recovery from Acidic Solutions", Journal of Hazardous Materials, 2013, vol. 263, pp. 391-397, XP055272716.

International Search Report for PCT International Application No. PCT/2016/022842, dated May 31, 2016, 5 pgs.

* cited by examiner

METHOD OF PURIFYING A BIOLOGICAL COMPOSITION AND ARTICLE THEREFOR

TECHNICAL FIELD

The present disclosure broadly describes methods and articles for purifying biological compositions using functionalized loose staple fibers.

BACKGROUND

Detection, quantification, isolation, and purification of target biomaterials such as viruses and biomacromolecules (e.g., including constituents or products of living cells, for example, proteins, carbohydrates, lipids, and nucleic acids) have long been objectives of investigators. Detection and quantification are important diagnostically, for example, as indicators of various physiological conditions such as diseases. Isolation and purification of biomacromolecules are important for therapeutic and in biomedical research. Biomacromolecules such as, for example, enzymes which are a special class of proteins capable of catalyzing chemical reactions are also useful industrially; enzymes have been isolated, purified, and then utilized for the production of sweeteners, antibiotics, and a variety of organic compounds such as ethanol, acetic acid, lysine, aspartic acid, and biologically useful products such as antibodies and steroids.

In their native state (i.e., in vivo), structures and corresponding biological activities of these biomacromolecules are maintained generally within fairly narrow ranges of pH and ionic strength. Consequently, any separation and purification operation must take such factors into account in order for the resultant, processed biomacromolecules to have potency.

Chromatographic separation and purification operations can be performed on biological product mixtures based on the interchange of a solute between a moving phase, which can be a gas or liquid, and a stationary phase. Separation of various solutes of the solution mixture is accomplished because of varying binding interactions of each solute with the stationary phase; stronger binding interactions generally result in longer retention times when subjected to the dissociation or displacement effects of a mobile phase compared to solutes which interact less strongly and, in this fashion, separation and purification can be effected. Column chromatography has been used to purify biological compositions; however, this technology is generally plagued by low throughput rates, channeling in the column packing, and/or high cost.

Polymeric resins are known for the separation and purification of various target compounds. For example, polymeric resins are used to purify or separate a target compound based on the presence of an ionic group, based on the size of the target compound, based on a hydrophobic interaction, based on an affinity interaction, or based on the formation of a covalent bond. Recently, ligand-functionalized substrates having such a polymeric coating on a substrate have been developed to aid in purification of biological compositions; for example, as disclosed in U.S. Pat. No. 8,377,672 B2 (Rasmussen et al.) and U.S. Pat. No. 8,435,776 B2 (Rasmussen et al.).

SUMMARY

While the two Rasmussen et al. patents described above may use ligand-functionalized fabrics for purification of a biological composition via a filtration process, the process can be slowed due to build up and clogging of pores in the fabric with cell debris, etc.

Advantageously, the present inventors have discovered a simple, faster method of purification by using loose ligand-functionalized staple fibers instead of a ligand-functionalized fabric.

In one aspect, the present disclosure provides a method of purifying a biological composition, the method comprising:

a) disposing loose cationic ligand-functionalized staple fibers and a biological composition within a mixing volume of a vessel, wherein the loose cationic ligand-functionalized staple fibers have a modified surface layer comprising a grafted acrylic polymer comprising 10 to 100 percent by weight of a cationically-ionizable monomer unit;

b) agitating the biological composition and the loose cationic ligand-functionalized staple fibers while they are in intimate contact with each other within the mixing volume to provide modified fibers and a purified biological composition; and c) separating at least a portion of the purified biological composition from the modified fibers and any loose cationic ligand-functionalized staple fibers with which it is in contact.

In another aspect, the present disclosure provides an article for purifying a biological composition.

The article comprises a specimen collection vessel having a mixing volume disposed therein; and loose cationic ligand-functionalized staple fibers disposed within the mixing volume, wherein the loose cationic ligand-functionalized staple fibers have a modified surface layer comprising a grafted acrylic polymer comprising 10 to 100 percent by weight of at least one cationically-ionizable monomer unit.

Advantageously and unexpectedly, methods of purifying a biological composition using loose cationic ligand-functionalized staple fibers according to the present disclosure, and articles that exploit the method, are capable of dramatically reducing the purification time for removing/isolating components of biological compositions as compared to prior methods involving similarly functionalized substrates.

The following definitions apply throughout the specification and claims.

The term "acrylic polymer" refers to a polymer containing at least 10 percent by weight (preferably at least 20, at least 30, at least 40, at least 50, at least 60, at least 70 or even at least 80 percent by weight) of monomer units independently represented by the formula wherein
R represents H or an alkyl group having from 1 to 4 carbon atoms, preferably one carbon atom; and
X represents the residue of an alcohol or an amine.

The term "biological composition" refers to any composition containing a macromolecule of biological origin. The composition need not be exclusively of biological origin. Examples include antibodies, cells, carbohydrates, RNA, DNA, and viruses.

The term "cationic ligand-functionalized" means having a functional group attached (e.g., indirectly or directly covalently bonded) thereto, wherein the functional group is either permanently cationic as in the case of a quaternary ammonium group, for example, or the group is sufficiently basic that it is substantially protonated in water having a pH of 5.0-8.0. For example, suitable such basic groups include groups with a $pK_a$ in water of their protonated cationic form of at least 9, preferably at least 10, and more preferably at least 12.5.

The term "cationically ionizable" means capable of forming an organic cation in water by dissociation (e.g., in the case of an onium salt) and/or protonation by the water (e.g., as in the case of an amine or guanidine).

The term "ionizable" means capable of spontaneously binding a proton to form a cationic species in water (e.g., at standard temperature and pressure).

The term "(meth)acryl" means "acryl and/or methacryl". Hence, methyl (meth)acrylate means methyl acrylate and/or methyl methacrylate.

The term "nonionizable" means substantially incapable (including incapable) of spontaneously acting as a Bronsted acid or base, or dissociating into ionic species, in water (e.g., at standard temperature and pressure).

The term "purify" means to increase the purity of, but not necessarily to isolate in pure form, unless otherwise specified.

Features and advantages of the present disclosure will be further understood upon consideration of the detailed description as well as the appended claims.

It should be understood that numerous other modifications and embodiments can be devised by those skilled in the art, which fall within the scope and spirit of the principles of the disclosure. The figure may not be drawn to scale.

DETAILED DESCRIPTION

The present disclosure concerns a method of purifying a biological composition that utilizes loose cationic ligand-functionalized staple fibers disposed in intimate contact with a biological composition within a mixing volume of a vessel. Methods and articles according to the present disclosure are suitable for use, especially in high ionic strength media, for removing and/or isolating near neutral or negatively-charged biological materials such as host cell proteins, DNA, RNA, viruses, and other microorganisms from the biological composition. Once bound to the cationic ligand-functionalized staple fibers, negatively-charged components of biological compositions can be removed by simple separation techniques such as, for example, collection of the fibers on a porous scrim or other substrate.

The loose cationic ligand-functionalized staple fibers are first of all staple fibers; that is, they are not continuous fibers. Preferably, the loose cationic ligand-functionalized staple fibers have a length of 0.1 mm to 2 cm, preferably 0.3 mm to 5 mm, and more preferably 0.5 mm to 3 mm; however, other lengths may also be used. The loose cationic ligand-functionalized staple fibers may be crimped or not crimped and/or fibrillated, for example.

As used herein, the term "loose" as applied to staple fiber means that the fiber is not formed into a paper, fabric, or twisted filament bundle (e.g., thread, yarn, or rope). The fibers may, however, be clumped together, although this is typically less preferred.

The loose cationic ligand-functionalized staple fibers can be prepared by grafting the acrylic polymer to the fiber according to known methods. The acrylic polymer can be made by polymerization of at least one acrylic monomer, optionally with at least one free-radically polymerizable monomer that is not an acrylic monomer. Free-radically polymerizable multifunctional monomers (e.g., having two or more free-radically polymerizable groups) may be included as well. The multifunctional monomers may be monomers having at least two free-radically polymerizable groups, or these may have a single free-radically polymerizable group and another polymerizable group (e.g., an epoxy group) that can reacted in a subsequent step after polymerization.

Examples of free-radically polymerizable acrylic monomers include hexyl(meth)acrylate, 2-ethylhexyl (meth)acrylate, isononyl (meth)acrylate, isobornyl (meth)acrylate, phenoxyethyl (meth)acrylate, 2-hydroxyethyl (meth)acrylate, dodecyl (meth)acrylate, methyl (meth)acrylate, ethyl (meth)acrylate, n-propyl (meth)acrylate, n-butyl (meth)acrylate, n-octyl (meth)acrylate, tetrahydrofurfuryl (meth)acrylate, isobutyl (meth)acrylate, cyclohexyl (meth)acrylate, octadecyl (meth)acrylate, (meth)acrylamide, dimethyl(meth)acrylamide, 2-hydroxyethyl(meth)acrylamide, and N-vinyl compounds such as, for example, N-vinylformamide, N-vinylpyrrolidone, and N-vinylcaprolactam. Acidic monomers such as acrylic acid, methacrylic acid, and (meth)acrylamidopropylsulfonic acid may also be used, but these may tend to interfere with performance of the loose cationic ligand-functionalized staple fibers and/or cause clumping of the fibers, and should typically be used judiciously, if at all, although this is not a requirement. Those monomers that are more hydrophilic or water soluble may be preferred in some embodiments due to their compatibility or solubility characteristics with the cationically-ionizable group containing acrylic monomer.

Examples of free-radically polymerizable monomers that are not acrylic monomers include alkenes, including halogenated alkenes, such as ethylene, propylene, isobutylene, hexene, isooctene, styrene, fluoroethylene, hexafluoropropylene, tetrafluoroethylene, vinylidene difluoride, chlorofluoroethylene, chlorotrifluoroethylene, and dichloroethylene. Allylic monomers may also be used. Examples include allyl ethers (e.g., allyl ethyl ether and allyl butyl ether), N-allylamides (e.g., N-allylacetamide and N-allylformamide), and allyl esters (e.g., allyl acetate, allyl benzoate, and allyl propanoate).

In one embodiment, useful free-radically polymerizable non-acrylic monomers may contain a cationically-ionizable group. In such cases, no acrylic monomer having a cationically-ionizable group is needed to form the grafted acrylic polymer.

Exemplary such free-radically polymerizable non-acrylic monomers include those represented by the formula wherein $R^1$ is H or an alkyl group having from 1 to 4 carbon atoms (e.g., methyl, ethyl, propyl, isopropyl, butyl), and $Z^-$ is a non-interfering anion (e.g., an anion that will not cause agglomeration of the cationic ligand-functionalized staple fibers or that tightly binds to the quaternary nitrogen atom, or that is oxidative toward the biological composition), preferably having a charge of −1, −2, or −3, more preferably −1. Preferred non-interfering anions include chloride and bromide.

Examples of free-radically polymerizable multifunctional monomers include glycidyl (meth) acrylate, methylenebis (meth)acrylamide, bis(meth)acryloylpiperazine, 1,3-butylene glycol di(meth)acrylate, 1,4-butanediol di(meth)acrylate, 1,6-hexanediol di(meth)acrylate, ethylene glycol di(meth)acrylate, alkoxylated aliphatic di(meth)acrylate, alkoxylated cyclohexanedimethanol di(meth)acrylate, alkoxylated hexanediol di(meth)acrylate, alkoxylated neopentyl glycol di(meth)acrylate, caprolactone modified neopentyl glycol hydroxypivalate di(meth)acrylate, caprolactone modified neopentyl glycol hydroxypivalate di(meth) acrylate, cyclohexanedimethanol di(meth)acrylate, diethylene glycol di(meth)acrylate, dipropylene glycol di(meth)acrylate, ethoxylated (10) bisphenol A di(meth) acrylate, ethoxylated (3) bisphenol A di(meth)acrylate, ethoxylated (30) bisphenol A di(meth)acrylate, ethoxylated (4) bisphenol A di(meth)acrylate, hydroxypivalaldehyde modified trimethylolpropane di(meth)acrylate, neopentyl glycol di(meth)acrylate, polyethylene glycol (200) di(meth) acrylate, polyethylene glycol (400) di(meth)acrylate, polyethylene glycol (600) di(meth)acrylate, propoxylated neopentyl glycol di(meth)acrylate, tetraethylene glycol di(meth) acrylate, tricyclodecanedimethanol di(meth)acrylate, triethylene glycol di(meth)acrylate, tripropylene glycol di(meth)acrylate; tri(meth)(meth)acrylates such as glycerol tri(meth)acrylate, trimethylolpropane tri(meth)acrylate, ethoxylated tri(meth)acrylates (e.g., ethoxylated (3) trimethylolpropane tri(meth)acrylate, ethoxylated (6) trimethylolpropane tri(meth)acrylate, ethoxylated (9) trimethylolpropane tri(meth)acrylate, ethoxylated (20) trimethylolpropane tri(meth)acrylate), pentaerythritol tri(meth)acrylate, propoxylated tri(meth)acrylates (e.g., propoxylated (3) glyceryl tri(meth)acrylate, propoxylated (5.5) glyceryl tri(meth) acrylate, propoxylated (3) trimethylolpropane tri(meth)acrylate, propoxylated (6) trimethylolpropane tri(meth)acrylate), trimethylolpropane tri(meth)acrylate, tris(2-hydroxyethyl) isocyanurate tri(meth)acrylate; and higher functionality (meth)acryl containing compounds such as ditrimethylolpropane tetra(meth)acrylate, dipentaerythritol penta(meth) acrylate, ethoxylated (4) pentaerythritol tetra(meth)acrylate, pentaerythritol tetra(meth)acrylate, caprolactone modified dipentaerythritol hexa(meth)acrylate, and combinations thereof. Again, for compatibility or solubility reason, the hydrophilic or water soluble multifunctional monomers are preferred.

If included, the amount of multifunctional monomer is typically less than 5 percent by weight of the free-radically polymerizable monomers used to make the grafted acrylic polymer, preferably less than 2 percent by weight, and more preferably less than 1 percent by weight; however, this is not a requirement.

Suitable fibers include fibers comprising synthetic polymers such as polyolefins (e.g., polyethylene, polypropylene, styrene-butadiene copolymers, polystyrene, and polyisobutylene, and combinations thereof); fluorinated polymers (e.g., homopolymers and copolymers of vinylidene difluoride, vinyl fluoride, tetrafluoroethylene, chlorotrifluoroethylene, combinations thereof, and copolymers of the foregoing with polyethylene and/or polypropylene); chlorinated polymers (e.g., polyvinylidene dichloride, polychloroprene, and polyvinyl chloride); polyesters (e.g., polycaprolactone and polyethylene terephthalate); polyamides (e.g., nylon-6,6 and nylon 6); vinyl acetate homopolymers and copolymers (e.g, with ethylene), and hydrolyzed derivatives thereof (e.g., poly(vinyl alcohol)); polyether sulfones; and polyimides. One preferred synthetic fiber is fibrillated high-density polyethylene (HDPE); for example, fibrillated HDPE fibers available from MiniFibers, Inc., Johnson City, Tenn., as SHORT STUFF FIBRILLATED HDPE (e.g., in grades ESS2F, ESS5F, ESS50F, E380F, E505F, E780F, E990F). Useful natural fibers include rayon, cellulose, cotton, linen, chitosan, and starch.

The fiber is surface-modified by grafting an acrylic polymer comprising 10 to 100 percent by weight of a cationically-ionizable monomer unit to its surface. Techniques for grafting acrylic polymers may involve subjecting the fibers to ionizing radiation (e.g., gamma radiation or electron beam radiation) and then contacting them with free-radically polymerizable monomers including acrylic monomers, wherein the entire process is carried out in an oxygen-free environment. Details of how to carry out such processes are described in numerous patents. Examples include U.S. Pat. No. 8,377,672 (Rasmussen et al.), U.S. Pat. No. 8,652,582 (Bothof et al.), U.S. Pat. No. 8,551,894 (Seshadri et al.), U.S. Pat. No. 8,328,023 (Weiss et al.), and U.S. Pat. No. 8,329,034 (Waller, Jr. et al.). Grafting of acrylic monomers may involve UV irradiation in the presence of a Type II photoinitiator, such as described in WO 2013/184366A1 (Bothof, et al.)

Loose cationic ligand-functionalized staple fibers have a modified surface layer comprising a grafted acrylic polymer. The grafted acrylic polymer comprises 10 to 100 percent by weight of a cationically-ionizable monomer unit. For example, the grafted acrylic polymer may contain at least 10 percent by weight, at least 20 percent by weight, at least 30 percent by weight, at least 40 percent by weight, or at least 50 percent by weight up to 60 percent by weight, 70 percent by weight, 80 percent by weight, 90 percent by weight, 95 percent by weight, or even 100 percent by weight of the cationically-ionizable monomer unit. Any cationically-ionizable monomer unit may be used. Preferred examples include divalent monomer units represented by any of the formulas (A) to (C), below:

(A)

R¹ represents H or an alkyl group having from 1 to 4 carbon atoms (e.g., methyl, ethyl, propyl, butyl, isopropyl). Preferably, R¹ is H or methyl.

R² represents a divalent alkylene group optionally substituted by a catenary carbonyloxy, carbonylamino, oxycarbonylamino, or ureylene divalent linking group. Preferably, R² has from 2 to 12 carbon atoms, more preferably 2 to 6 carbon atoms, and more preferably 2 to 4 carbon atoms.

Each R³ independently represents H or an alkyl group having from 1 to 4 carbon atoms (e.g., methyl, ethyl, propyl, butyl, isopropyl). Preferably, R³ is H, methyl, or ethyl.

R⁴ represents H, an alkyl group having from 1 to 4 carbon atoms (e.g., methyl, ethyl, propyl, butyl, isopropyl), or —N(R³)₂ wherein R³ is as defined above. Preferably, R⁴ is H, methyl, or ethyl.

X¹ represents —O— or —NR³— wherein R³ is as defined above.

Preferred examples also include divalent monomer units represented by formulas (D) or (E), below:

wherein

R⁵ is H, C₁-C₁₂ alkyl, or C₅-C₁₂ (hetero)aryl;

R⁶ is a covalent bond, C₂-C₁₂ alkylene, C₅-C₁₂ (hetero)arylene, each R⁷ is independently H, —OH, C₁-C₁₂ alkyl, or C₅-C₁₂ (hetero)aryl, preferably H or C₁-C₄ alkyl;

R⁸ is H, C₁-C₁₂ alkyl, C₅-C₁₂ (hetero)aryl, or —N(R⁷)₂, preferably H or C₁-C₄ alkyl R⁹ is C₂-C₁₂ alkylene or C₅-C₁₂ (hetero)arylene;

X² is —O— or —NR⁷—;

R¹⁰ is C₂-C₁₂ alkylene; and

R¹¹ is H or methyl.

Further details concerning divalent monomer units and methods for their preparation can be found in U.S. Pat. No. 8,377,672 (Rasmussen).

Monomeric units (A) and (B) may be conveniently generated by polymerization of corresponding monomers, or by reaction of a pendant reactive group such as an azlactone group of a precursor polymer (e.g., a polymer made from monomers including an alkenylazlactone), for example, with a primary or secondary aminoalkyl-functional guanidine or agmatine compound. Monomers and methods suitable for generating the monomeric units (A) and (B) are described, for example, in U.S. Pat. No. 8,377,672 (Rasmussen et al.), U.S. Pat. No. 8,652,582 (Bothof et al.), and WO 2014/204763A1 (Rasmussen, et al.).

Examples of suitable monomers for generating monomeric unit (C) include salts (e.g., chloride or bromide salts) of N-(3-trimethylammoniopropypacrylamide; 2-trimethylammonioethyl methacrylate; 2-trimethylammonioethyl acrylate; N-(3-trimethylammoniopropyl)methacrylamide; N-(6-trimethylammoniohexyl)acrylamide; and N-(3-trimethylammoniopropyl)acrylamide. Monomers and methods suitable for generating the monomeric unit (C) can be found, for example, in U.S. Pat. No. 6,007,803 (Mandeville, III et al.) and in PCT International Pat. Appl. No. US2014/057388, filed Sep. 25, 2014. Cationic monomeric unit (C) is preferably paired with a non-interfering anion Z⁻ as defined previously.

Cationically-ionizable monomer units may be generated for example as a result of free-radical polymerization (e.g., homopolymerization or copolymerization) of a corresponding monomer having a cationically-ionizable group, or by polymerization (e.g., homopolymerization or copolymerization) of a precursor monomer that is functionalized with a cationically-ionizable group in a subsequent reaction.

The grafted acrylic polymer may further comprise 0.1 to 90 percent by weight of at least one nonionizable hydrophilic monomer unit, or it may contain none at all. For example, the grafted acrylic polymer may contain at least 1 percent by weight, at least 5 percent by weight, at least 10 percent by weight, at least 15 percent by weight, or at least 25 percent by weight up to 30 percent by weight, 40 percent by weight, 50 percent by weight, 75 percent by weight, or 90 percent by weight of the at least one nonionizable hydrophilic monomer unit. In some embodiments, the nonionizable hydrophilic monomer unit comprises a divalent residue of an N-vinyllactam having from 5 to 7 carbon atoms as shown below, wherein n=1, 2, or 3.

Such monomeric units can be readily introduced by including N-vinylpyrrolidone, N-vinylvalerolactam, and/or N-vinylcaprolactam in the monomers that are polymerized to prepare the grafted acrylic polymer.

In some embodiments, the nonionizable hydrophilic monomer unit comprises a divalent residue of a polyether (meth)acrylate as shown below, wherein $R^1$ and $R^3$ are as previously defined and w is an integer≥2.

Such monomeric units can be readily introduced by including polyether (meth)acrylates in the monomers that are polymerized to prepare the grafted acrylic polymer. Methods of making such monomers are well-known in the art and many are commercially available. Examples include 2-(2-ethoxyethoxy)ethyl acrylate, methoxypolyethylene glycol (350) monoacrylate, methoxypolyethylene glycol (350) monomethacrylate, methoxypolyethylene glycol (550) monoacrylate, and methoxypolyethylene glycol (550) monomethacrylate, all available from Sartomer Co., Exton, Pa.

Optionally, the biological composition may be pretreated with a water-soluble polymeric flocculant that flocculates a portion of the components of the biological composition prior to (or simultaneously with) combining it with the loose cationic ligand-functionalized staple fibers. Examples of suitable flocculants include cationic ligand-functionalized synthetic polymers, for example, as disclosed in U. S. Pat. No. 8,377,672 (Rasmussen et al.) and U.S. Pat. No. 8,435,776 (Rasmussen et al.). Suitable vessels comprise at least one mixing volume (e.g., a chamber). Exemplary vessels include specimen collection tubes and bags (preferably sealed specimen collection tubes and bags), mixing vessels with drains, flasks, beakers, barrels, bags, troughs, tubular flow reactors, static mixers, and vats. In some embodiments, the vessel is closed and/or sealed (e.g., with rubber septum/ stopper or cap). Suitable vessels may be disposable or reusable, for example. Stirring devices (e.g., paddles, agitators, propellers, or stir bars) may be used in conjunction with the mixing vessels to facilitate agitation.

Static mixers (e.g., as shown schematically in FIG. 2) are commercially available from various suppliers such, for example, Koflo Corp., Cary, Ill., and Charles Ross and Son Co., Hauppauge, N.Y. In some embodiments, the vessel is fitted with a drain, operable by opening and closing a valve (e.g., a stopcock). This may be particularly useful with larger vessels that cannot be manipulated easily by hand.

Figure 1:
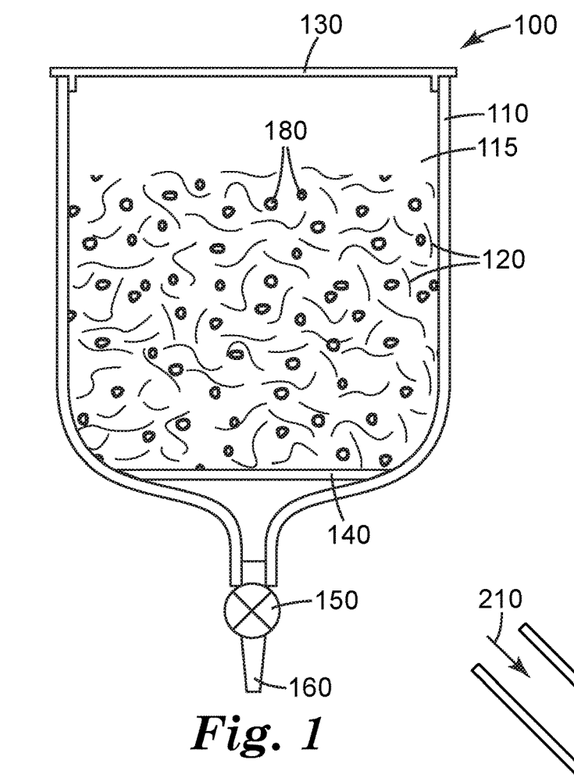
FIG. 1 is a schematic cross-sectional side view of an exemplary article 100 according to the present disclosure.

Referring now to FIG. 1, exemplary article 100 purifying a biological composition comprises vessel 110 having mixing volume 115 disposed therein. Loose cationic ligand-functionalized staple fibers 120 according to the present disclosure are disposed within mixing volume 115. Optional cover 130 (e.g., a rubber septum, plastic press-fit top, or screw top), together with vessel 100, encloses mixing volume 115. Optionally, synthetic polymeric flocculent particles 180 may also be present.

In use, a biological composition (not shown) is disposed in the mixing volume, the fibers 120 and the biological composition are agitated while in intimate contact. Optional valve 150 may be opened allowing the purified biological composition to drain through porous substrate 140 and flow through optional outlet port 160.

Figure 2:
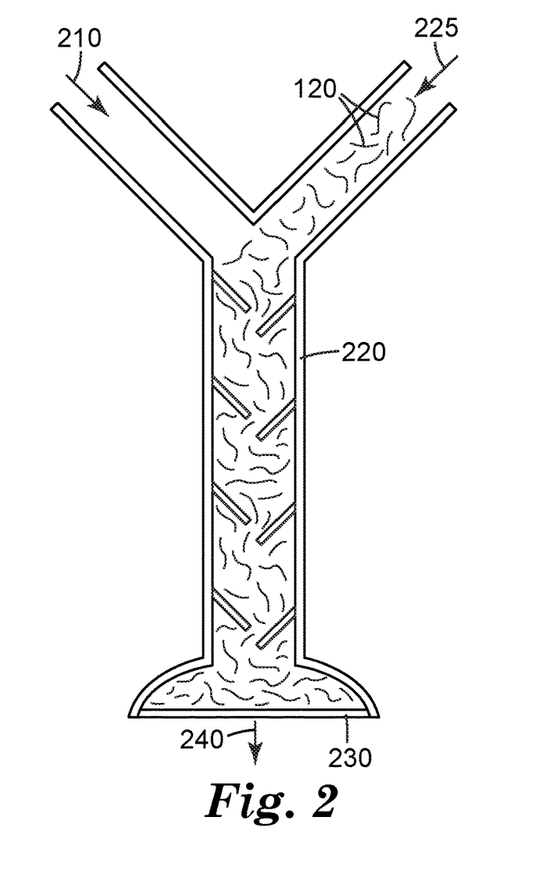
FIG. 2 is a schematic process flow diagram of an exemplary embodiment of a method according to the present disclosure.

One exemplary embodiment for carrying out a method according to the present disclosure is shown in FIG. 2. Referring now to FIG. 2, loose cationic ligand-functionalized staple fibers 120 are suspended in a fluid 225 (e.g., saline or water), optionally containing dissolved synthetic polymer flocculent, are combined with biological composition 210 and passed through static mixer 220. Particulate and fiber materials are removed by porous filter 230 and purified biological composition 240 passes through porous filter 230 to be collected.

The loose cationic ligand-functionalized staple fibers may be disposed within the mixing chamber before, after, or simultaneously with, disposing the biological composition within the mixing chamber of the vessel.

Once combined in the mixing vessel, the biological composition and the loose cationic ligand-functionalized staple fibers are agitated while they are in intimate contact with each other within the mixing chamber to provide modified fibers (i.e., having some material(s) from the biological composition bound thereto) and a purified biological composition. Suitable mixing methods include shaking by hand, laboratory agitators, mechanical and/or magnetic stirrers, and passing through a static mixer, for example. Agitation may be performed for any length of time sufficient to effectively bind biological compounds to the fibers. In some embodiments, the agitation is preferably less than 60 seconds, less than 45 seconds, or even less than 30 seconds. In other embodiments, the agitation may be as long as 20 minutes or more, for example.

Separation of the purified biological composition from the modified fibers may be accomplished by any suitable method including, for example, centrifugation, decanting, filtration, and sieving. In one particularly preferred embodiment, the contents of the mixing chamber, after agitating them, are transported through a porous substrate (e.g., a porous scrim, porous membrane, porous nonwoven fabric, or mesh), whereby the fibers do not pass through the porous substrate and form a porous mat of fibers disposed upstream from the substrate, and which may serve to mechanically remove particulate debris remaining in the purified biological composition. Polypropylene, polyethylene, metal, and glass may be used as materials for the porous substrate, for example.

Typically the porous substrate has openings/pores of from about 0.5 mm to about 0.5 cm in order to achieve efficient collection of the modified fibers without excessively impeding fluid flow through the porous substrate, although other opening/pore sizes may also be used.

In some embodiments, the biological species being removed from the fluid is the object of the purification. For example, a recombinant protein or enzyme may be prepared in cell culture, the loose cationic ligand-functionalized staple fibers can be added to flocculate the protein or enzyme, and the precipitate can be separated as the first step in the purification process for the protein or enzyme. In another example, the loose cationic ligand-functionalized staple fibers may be used to capture microorganisms from a fluid as the first step in a process of concentrating, enumerating, and/or identifying the microorganisms.

In other embodiments, the biological species being removed from the fluid is a contaminant that must be removed prior to additional processing steps for the fluid.

Accordingly, the loose cationic ligand-functionalized staple fibers can be used to bind and facilitate the removal of cells and cell debris from a biological composition such as, for example, a cell culture or fermentation broth. It can be used to precipitate either desired or contaminating proteins or nucleic acids from solution. Significantly, the loose cationic ligand-functionalized staple fibers are useful under conditions of high salt concentration or high ionic strength.

Select Embodiments of the Present Disclosure

In a first embodiment, the present disclosure provides a method of purifying a biological composition, the method comprising:
a) disposing loose cationic ligand-functionalized staple fibers and a biological composition within a mixing volume of a vessel, wherein the loose cationic ligand-functionalized staple fibers have a modified surface layer comprising a grafted acrylic polymer comprising 10 to 100 percent by weight of a cationically-ionizable monomer unit;
b) agitating the biological composition and the loose cationic ligand-functionalized staple fibers while they are in intimate contact with each other within the mixing volume to provide modified fibers and a purified biological composition; and
c) separating at least a portion of the purified biological composition from the modified fibers and any loose cationic ligand-functionalized staple fibers with which it is in contact.

In a second embodiment, the present disclosure provides a method according to the first embodiment, wherein the loose cationic ligand-functionalized staple fibers are disposed within the mixing volume before the biological composition is disposed within the mixing volume.

In a third embodiment, the present disclosure provides a method according to the first or second embodiment, wherein step b) is accomplished at least in part using a static mixer.

In a fourth embodiment, the present disclosure provides a method according to any one of the first to third embodiments, wherein at least a portion of the loose cationic ligand-functionalized staple fibers are fibrillated.

In a fifth embodiment, the present disclosure provides a method according to any one of the first to fourth embodiments, wherein the biological composition contains a synthetic polymer flocculant.

In a sixth embodiment, the present disclosure provides a method according to the fifth embodiment, wherein the grafted acrylic polymer further comprises a multifunctional monomer unit.

In a seventh embodiment, the present disclosure provides a method according to any one of the first to sixth embodiments, wherein the grafted acrylic polymer further comprises 0.1 to 90 percent by weight of at least one nonionizable hydrophilic monomer unit.

In an eighth embodiment, the present disclosure provides a method according to the seventh embodiment, wherein the nonionizable hydrophilic monomer unit comprises an N-vinyllactam having from 4 to 6 carbon atoms.

In a ninth embodiment, the present disclosure provides a method according to any one of the first to eighth embodiments, wherein the cationically-ionizable monomer unit is a divalent monomer unit represented by the formula:

wherein:
R$^1$ is H or an alkyl group having from 1 to 4 carbon atoms;
R$^2$ is a divalent alkylene group optionally substituted by a catenary carbonyloxy, carbonylamino, oxycarbonylamino, or ureylene divalent linking group;
each R$^3$ independently is H or an alkyl group having from 1 to 4 carbon atoms;
R$^4$ is H or an alkyl group having from 1 to 4 carbon atoms or —N(R$^3$)$_2$; and
X$^1$ is —O— or —NR$^3$—.

In a tenth embodiment, the present disclosure provides a method according to any one of the first to eighth embodiments, wherein the cationically-ionizable monomer unit comprises a divalent monomer unit represented by the formula:

wherein:
R$^1$ is H or an alkyl group having from 1 to 4 carbon atoms;
R$^2$ is a divalent alkylene group optionally substituted by a catenary carbonyloxy, carbonylamino, oxycarbonylamino, or ureylene divalent linking group; and
each R$^3$ independently is H or an alkyl group having from 1 to 4 carbon atoms; R$^4$ is H or an alkyl group having from 1 to 4 carbon atoms or —N(R$^3$)$_2$; and
X$^1$ is —O— or —NR$^3$—.

In an eleventh embodiment, the present disclosure provides a method according to the first to tenth embodiments, wherein the vessel comprises an optionally sealed specimen collection bag or tube.

In a twelfth embodiment, the present disclosure provides a method according to the any one of the first to eleventh embodiments, wherein step c) includes depositing at least a portion of the modified fibers and any loose cationic ligand-functionalized staple fibers on a porous substrate.

In a thirteenth embodiment, the present disclosure provides an article for purifying a biological composition, the article comprising:

a vessel having a mixing volume disposed therein; and loose cationic ligand-functionalized staple fibers disposed within the mixing volume, wherein the loose cationic ligand-functionalized staple fibers have a modified surface layer comprising a grafted acrylic polymer comprising 10 to 100 percent by weight of at least one cationically-ionizable acrylic monomer unit.

In a fourteenth embodiment, the present disclosure provides an article according to the thirteenth embodiment, wherein the grafted acrylic polymer comprises a multifunctional monomer unit.

In a fifteenth embodiment, the present disclosure provides an article according to the thirteenth or fourteenth embodiment, wherein the grafted acrylic polymer further comprises 0.1 to 90 percent by weight of at least one nonionizable hydrophilic monomer unit.

In a sixteenth embodiment, the present disclosure provides an article according to the fifteenth embodiment, wherein the nonionizable hydrophilic monomer unit comprises an N-vinyllactam having from 4 to 6 carbon atoms.

In a seventeenth embodiment, the present disclosure provides an article according to any one of the thirteenth to sixteenth embodiments, wherein the cationically-ionizable acrylic monomer unit is represented by the formula:

wherein:
$R^1$ is H or an alkyl group having from 1 to 4 carbon atoms;
$R^2$ is a divalent alkylene group optionally substituted by a catenary carbonyloxy, carbonylamino, oxycarbonylamino, or ureylene divalent linking group;
each $R^3$ is independently H or an alkyl group having from 1 to 4 carbon atoms;
$R^4$ is H or an alkyl group having from 1 to 4 carbon atoms or —$N(R^3)_2$; and
$X^1$ is —O— or —$NR^3$—.

In an eighteenth embodiment, the present disclosure provides an article according to any one of the thirteenth to sixteenth embodiments, wherein the cationically-ionizable monomer unit comprises a divalent monomer unit represented by the formula:

wherein:
$R^1$ is H or an alkyl group having from 1 to 4 carbon atoms;
$R^2$ is a divalent alkylene group optionally substituted by a catenary carbonyloxy, carbonylamino, oxycarbonylamino, or ureylene divalent linking group; and
each $R^3$ independently is H or an alkyl group having from 1 to 4 carbon atoms.

In a nineteenth embodiment, the present disclosure provides an article according to any one of the thirteenth to eighteenth embodiments, wherein at least a portion of the loose cationic ligand-functionalized staple fibers are fibrillated.

In a twentieth embodiment, the present disclosure provides an article according to any one of the thirteenth to nineteenth embodiments, wherein the biological composition contains a synthetic polymer flocculant.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages (%), ratios, etc. in the Examples and the rest of the specification are by weight. Materials used in the examples are available from standard chemical vendors (e.g., such as Sigma-Aldrich Co., Saint Louis, Mo.) and/or prepared according to known methods, unless otherwise indicated. Materials abbreviations used in the Examples are listed in Table 1, below.

TABLE 1

| ABBRE-VIATION | DESCRIPTION |
|---|---|
| NVP | N-vinylpyrrolidone |
| IEM-Ag | 4-(2-(methacryloyloxy)ethylaminocarbonylamino) butyl guanidinium sodium sulfate prepared according to the procedure of Example 99, paragraph [0151] of US 2012/0252091 A1 (Rasmussen et al.) |
| GMA | glycidyl methacrylate |
| MAPTAC | 3-methacrylamidopropyltrimethylammonium chloride |

Preparative Example 1 (PE 1)

Ten grams of polyethylene (PE) fibers (SHORT STUFF E380F, ~0.7 mm in length and 0.015 mm diameter, obtained from Minifibers Inc., Johnson City, Tenn.) were purged with nitrogen in an oxygen depleted (<50 ppm oxygen) glove box. The fibers were sealed in a plastic bag and removed from the glove box. The fibers were irradiated by passing under a BROADBEAM EP e-beam apparatus from PCT Engineered Systems, Davenport, Iowa, at 10 Mrad and 300 kV. The bag was then flipped over and again passed through the e-beam at 10 Mrad and 300 kV. The bag was then returned to the nitrogen purged glove box.

The irradiated fibers were transferred to a glass jar and coated with 223 g of a monomer-containing coating solution containing 11.1 wt. % of NVP, 6.7 wt. % of IEM-Ag, 5 wt. % of GMA, and 77.2 wt. % of deionized water. The fibers and monomers were allowed to react overnight in the nitrogen purged glove box.

The reacted fibers were washed three times with 14 mM sodium chloride water, allowing the salt water to drain through a screen mesh while retaining the fibers. The fibers were then transferred to a large aluminum pan and allowed to dry. The dried fibers were weighed to determine the final graft yield. The washed fibers weighed 41.9 g, indicating that 31.9 g of grafted polymer had been added to the 10 g of fibers.

Preparative Examples 2 and 3 (PE2 and PE3)

The procedure of Example 1 was used to produce functionalized fibers, except that the PE fiber was SHORT STUFF E780F, 1.3-2 mm length, 0.025 mm diameter, and the amounts of individual components were varied as reported in Table 2. The fibers were used for Examples 2 and 3.

were immediately vacuum filtered at a max pressure of 18-20 in. Hg (61-68 kPa) (Model 2522B-01 vacuum pump, Welch-Ilmvac, Niles, Ill.) through a polypropylene blown microfiber nonwoven filter (basis weight=107 g/m$^2$, 5.9 percent solidity, and 37.8 micrometers effective fiber diameter) using a 25 mm glass vacuum filter holder (Millipore). As a comparison, the same amount of fibers were prepacked by mixing with 10 mL of phosphate-buffered saline, pH 7.4 (available from Life Technologies) and vacuum filtered onto the base substrate. After packing the fiber mat, CHO culture (15 ml) was added and vacuum filtered. For all samples, sample filtration time was determined from starting a stopwatch when turning on the vacuum pump and stopping the pump when the solution ran through and a dry fiber mat remained. Contact time was determined for each sample and refers to the total amount of time the fibers were in contact with a biological solution. It was estimated as the time from when the biological solution was added to the fibers, mixed, poured into the filtration funnel, and filtered through the base substrate. The filtrate was collected for further analysis (turbidity, DNA concentration, host cell protein concentration).

Turbidity of the filtrate was determined my measuring the filtrate using a Hach 2100AN Turbidimeter (Hach Co., Loveland, Colo.). A 1-mL aliquot of sample filtrate was centrifuged at 14000 rpm for 5 min to remove non-soluble material. Total protein, DNA and CHO host cell protein

TABLE 2

| EXAMPLE | COATING SOLUTION, g | FIBER, g | LIGAND | WT. % OF LIGAND | WT. % OF NVP | WT. % OF GMA | WT. % OF WATER | GRAFT ADD-ON, g polymer/ g fiber |
|---|---|---|---|---|---|---|---|---|
| PE1 | 223 | 10 g of 380F | IEM-Ag | 6.7 | 11.1 | 5 | 77.2 | 3.19 |
| PE2 | 116.5 | 5 g of 780F | IEM-Ag | 6.7 | 11.1 | 5 | 77.2 | 4.12 |
| PE3 | 116.5 | 5 g of 780F | MAPTAC | 6.7 | 11.1 | 5 | 77.3 | 3.33 |

Examples 5-6 and Comparative Examples A-C

Chinese hamster ovary (CHO) culture (available as CHO-S from Life Technologies, Grand Island, N.Y.) was grown in CD CHO media (available from Life Technologies) with appropriate supplements, at 37° C. in a humidified atmosphere of 5% $CO_2$, by volume, in air.

Fifteen milliliters of the culture was added to 15 mL conical tubes containing 320 mg of the IEM-agmatine functionalized fibers of Example 1, and then mixed by hand for 10 sec or 10 minutes on a rotator. After mixing, samples (CHOP) concentrations were determined from the centrifugate using a Coomassie Plus protein assay (available from Life Technologies), a QUANT IT PICOGREEN DSDNA assay kit (Life Technologies), and a CHO HCP ELISA kit (Cygnus Technologies, Southport, N.C.), respectively, by following the manufacturer's protocol. Samples were performed in triplicate, except for the starting culture (n=1), to show a representative starting baseline, and the results are reported in Table 3, below, wherein "NA" means "not applicable".

TABLE 3

| EXAMPLE | SAMPLE | FIBER MASS, mg | FILTER TIME, sec | EST. CONTACT TIME, sec | TURBIDITY, NTU | [DNA], nanogram/mL | [Protein], microgram/mL | [CHOP], microgram/mL |
|---|---|---|---|---|---|---|---|---|
| Comp. Ex. A | Starting culture | NA | NA | NA | 148.4 | 893 | 127.3 | 25.4 |
| Comp. Ex. B | Filtered culture (no fiber) | 0 | 2.7 | NA | 143.1 | 2142 | 204.9 | 27.8 |
| Comp. Ex. C | Prepacked: PE1 fibers | 317 | 20.1 | 20.1 | 13.9 | 315 | 95.1 | 13.5 |
| 5 | Fibers - 10 sec mix: PE1 fibers | 322 | 2.8 | 12.8 | 47.5 | 321 | 139.6 | 20.5 |
| 6 | Fibers - 10 min mix: PE1 fibers | 327 | 2.6 | 602.6 | 27.5 | 23 | 99.8 | 15.0 |

Examples 7-10 and Comparative Examples D-G

Examples 7-10 and comparative examples D-G were carried out similarly to Examples 5-6 and Comparative examples A-C above, with the following modifications: i) a new CHO culture was used; ii) fibers and biological solution were mixed in a 50 mL conical tube instead of 15 mL tubes; and iii) mixing time was changed to match the contact time between the free fiber sample and the prepacked fiber media.

Samples were performed in triplicate, except for the starting culture (n=1) to show a representative starting baseline, and the results are reported in Table 4, below.

TABLE 4

| EXAMPLE | SAMPLE | FIBER MASS, mg | FILTER TIME, sec | EST. CONTACT TIME, sec | TUR-BIDITY, NTU | [DNA], nano-gram/mL | [Protein], micro-gram/mL |
|---|---|---|---|---|---|---|---|
| Comp. Ex. D | Starting culture | NA | NA | NA | 174.2 | 168.4 | 786.2 |
| Comp. Ex. E | Filtered culture (no fiber) | 0 | 2.2 | 0.0 | 171.8 | 165.7 | 784.6 |
| Comp. Ex. F | Prepacked: PE2 fibers | 256 | 3.2 | 5.2 | 40.2 | 94.4 | 682.7 |
| 7 | Fibers - 1 sec mix: PE2 fibers | 251 | 2.3 | 5.3 | 25.4 | 85.3 | 701.0 |
| 8 | Fibers - 10 min mix: PE2 fibers | 245 | 1.8 | 602.8 | 12.4 | 2.3 | 539.7 |
| Comp. Ex. G | Prepacked: PE3 fibers | 211 | 4.0 | 6.0 | 12.2 | 65.5 | 705.4 |
| 9 | Fibers - 1 sec mix: PE3 fibers | 223 | 2.9 | 5.9 | 36.4 | 52.2 | 739.0 |
| 10 | Fibers - 10 min mix: PE3 fibers | 219 | 2.1 | 603.1 | 18.6 | 2.0 | 669.8 |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A method of purifying a biological composition, the method comprising:
    a) disposing loose cationic ligand-functionalized staple fibers and a biological composition within a mixing volume of a vessel, wherein the loose cationic ligand-functionalized staple fibers have a modified surface layer comprising a grafted acrylic polymer comprising 10 to 100 percent by weight of a cationically-ionizable monomer unit, and wherein at least a portion of the loose cationic ligand-functionalized staple fibers are fibrillated high-density polyethylene fibers;
    b) agitating the biological composition and the loose cationic ligand-functionalized staple fibers while they are in intimate contact with each other within the mixing volume to provide modified fibers and a purified biological composition; and
    c) separating at least a portion of the purified biological composition from the modified fibers and any loose cationic ligand-functionalized staple fibers with which it is in contact.

2. The method of claim 1, wherein the loose cationic ligand-functionalized staple fibers are disposed within the mixing volume before the biological composition is disposed within the mixing volume.

3. The method of claim 1, wherein step b) is accomplished at least in part using a static mixer.

4. The method of claim 1, wherein the biological composition contains a synthetic polymer flocculant.

5. The method of claim 1, wherein the grafted acrylic polymer further comprises a multifunctional monomer unit.

6. The method of claim 1, wherein the grafted acrylic polymer further comprises 0.1 to 90 percent by weight of at least one nonionizable hydrophilic monomer unit.

7. The method of claim 6, wherein the nonionizable hydrophilic monomer unit comprises an N-vinyllactam having from 4 to 6 carbon atoms.

8. The method of claim 1, wherein the cationically-ionizable monomer unit is a divalent monomer unit represented by the formula:

wherein:
    $R^1$ is H or an alkyl group having from 1 to 4 carbon atoms;
    $R^2$ is a divalent alkylene group optionally substituted by a catenary carbonyloxy, carbonylamino, oxycarbonylamino, or ureylene divalent linking group;
    each $R^3$ independently is H or an alkyl group having from 1 to 4 carbon atoms;
    $R^4$ is H or an alkyl group having from 1 to 4 carbon atoms or $-N(R^3)_2$; and
    $X^1$ is $-O-$ or $-NR^3-$.

9. The method of claim 1, wherein the cationically-ionizable monomer unit comprises a divalent monomer unit represented by the formula:

wherein:
R$^1$ is H or an alkyl group having from 1 to 4 carbon atoms;
R$^2$ is a divalent alkylene group optionally substituted by a catenary carbonyloxy, carbonylamino, oxycarbonylamino, or ureylene divalent linking group; and
each R$^3$ independently is H or an alkyl group having from 1 to 4 carbon atoms.

10. The method of claim 1, wherein the vessel comprises a sealed specimen bag.

11. The method of claim 1, wherein step c) includes depositing at least a portion of the modified fibers and any loose cationic ligand-functionalized staple fibers on a porous substrate.

12. An article for purifying a biological composition, the article comprising:
a vessel having a mixing volume disposed therein; and
loose cationic ligand-functionalized staple fibers disposed within the mixing volume, wherein the loose cationic ligand-functionalized staple fibers have a modified surface layer comprising a grafted acrylic polymer comprising 10 to 100 percent by weight of at least one cationically-ionizable acrylic monomer unit, and wherein at least a portion of the loose cationic ligand-functionalized staple fibers are fibrillated high-density polyethylene fibers.

13. The article of claim 12, wherein the grafted acrylic polymer comprises a multifunctional monomer unit.

14. The article of claim 13, wherein the grafted acrylic polymer further comprises 0.1 to 90 percent by weight of at least one nonionizable hydrophilic monomer unit.

15. The article of claim 14, wherein the nonionizable hydrophilic monomer unit comprises an N-vinyllactam having from 4 to 6 carbon atoms.

16. The article of claim 12, wherein the cationically-ionizable acrylic monomer unit is represented by the formula:

wherein:
R$^1$ is H or an alkyl group having from 1 to 4 carbon atoms;
R$^2$ is a divalent alkylene group optionally substituted by a catenary carbonyloxy, carbonylamino, oxycarbonylamino, or ureylene divalent linking group;
each R$^3$ is independently H or an alkyl group having from 1 to 4 carbon atoms;
R$^4$ is H or an alkyl group having from 1 to 4 carbon atoms or —N(R$^3$)$_2$; and
X$^1$ is —O— or —NR$^3$—.

17. The article of claim 12, wherein the cationically-ionizable monomer unit comprises a divalent monomer unit represented by the formula:

wherein:
R$^1$ is H or an alkyl group having from 1 to 4 carbon atoms;
R$^2$ is a divalent alkylene group optionally substituted by a catenary carbonyloxy, carbonylamino, oxycarbonylamino, or ureylene divalent linking group; and
each R$^3$ independently is H or an alkyl group having from 1 to 4 carbon atoms.

18. The article of claim 12, wherein the biological composition contains a synthetic polymer flocculant.

* * * * *

UNITED STATES PATENT AND TRADEMARK OFFICE
CERTIFICATE OF CORRECTION

PATENT NO. : 10,562,997 B2
APPLICATION NO. : 15/549268
DATED : February 18, 2020
INVENTOR(S) : Vail et al.

Page 1 of 1

It is certified that error appears in the above-identified patent and that said Letters Patent is hereby corrected as shown below:

In the Specification

<u>Column 6</u>
Line 6, Delete "(e.g," and insert -- (e.g., --, therefor.

<u>Column 8</u>
Line 29, Delete "-trimethylammoniopropypacrylamide;" and insert
-- -trimethylammoniopropyl)acrylamide; --, therefor.

Signed and Sealed this
Fifteenth Day of September, 2020

Andrei Iancu
*Director of the United States Patent and Trademark Office*